US006347632B1

United States Patent
Eberhardt et al.

(10) Patent No.: US 6,347,632 B1
(45) Date of Patent: *Feb. 19, 2002

(54) COMPLIANT SIMULATED AORTAS, METHOD FOR MAKING SAME BY ADJUSTING DUROMETER OF MATERIALS, AND METHOD FOR TESTING HEART VALVES

(75) Inventors: Carol E. Eberhardt, Fullerton; David J. Myers, Garden Grove, both of CA (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 07/910,970

(22) Filed: Jul. 9, 1992

(51) Int. Cl.$^7$ .............................................. A61B 19/00
(52) U.S. Cl. ...................... 128/898; 623/1.1; 623/66.1
(58) Field of Search ................ 623/1.13, 1.29, 623/1.26, 2.1, 2.36, 2.38, 66.1, 1.1; 128/898; 73/866.4

(56) References Cited

U.S. PATENT DOCUMENTS

| 4,767,418 A | 8/1988 | Deininger et al. ............. 623/1 |
| 5,139,515 A | 8/1992 | Robicsek ....................... 623/1 |

FOREIGN PATENT DOCUMENTS

| WO | 8901765 | 3/1989 |
| WO | 9219199 | 11/1992 |

OTHER PUBLICATIONS

Optimal Design of Aortic Leaflet Prosthesis, *Journal of the Engineering Mechanics Division,* By Dhanjoo N. Ghista, Helmut Reul, Gautam Ray, and K.B. Chandran, Feb. 1978, pp. 97–117.

Optimal Prosthetic Aortic Leaflet Valve: Design Parametric and Longevity Analyses: Development of the Avcothane–51 Leaflet Valve Based on the Optimum Design Analysis, *Journal of Biomechanics,* 10/5–6, 1977 pp. 313–324.

Measurement of Turbulence in Aortic Valve Prostheses: An Assessment by Laser Doppler Anemometer, *Proceedings of a Symposium at the 14th Annual Meeting of the Association for the Advancement of Medical Instrumentation,* P.C. Lu, A.M. Sallam, and N.H.C. Hwang, Las Vegas, NV, May 21, 1979.

Normal Aortic Valve Function in Dogs, *The American Journal of Cardiology,* Mano Thubrikar, PhD, Robert Harry, MD, Stanton P. Nolan, MD, FACC, Oct. 1977, vol. 40, pp. 563–568.

The Dynamic Aortic Root, *Journal of Thorac Cardiovascular Surgery,* Richard J. Brewer, M.D., David Deck, PhD, Bienvenido Capati, MD, and Stanton P. Nolan, MD., Sep. 1976, 72(3): pp. 413–417.

(List continued on next page.)

Primary Examiner—Dinh X. Nguyen
(74) Attorney, Agent, or Firm—Daniel W. Latham, Esq.; Timothy A. Czaja, Esq.

(57) ABSTRACT

A method of creating a simulated aorta patterned from a natural aorta and having a preselected amount of compliance is disclosed. The dimensions of a simulated aortic root patterned according to the dimensions of a natural aorta are first selected and a mold provided. The amount of circumferential compliance desired in the simulated aorta is then selected, based on natural circumferential compliancies. A material such as silicone rubber formed of an elastomer and a filler is used to form the aorta, the durometer of the material being varied by varying the relative amount of the components, to provide the selected amount of circumferential compliance in a simulated aorta having the selected dimensions. The aorta is then formed curing the material in the mold for about 24 hours. Groups of simulated aortas so produced, sometimes having different sizes and/or compliancies are also disclosed. A method of testing non-stented valves using the aortas is included.

13 Claims, 6 Drawing Sheets

OTHER PUBLICATIONS

Assessment of Aortic Pressure–Volume Relationships with an Impedance Catheter, *Catheterization and Cardiovascular Diagnosis,* 15:27–36 (1988), by Jmaes J. Ferguson, III, MD, Michael J. Miller, MD, Peter Sahagian, BA, Julian M. Aroesty, MD and Raymond G. McKay, MD.

Two–Dimensional Echocardiographic Aortic Root Dimensions in Normal Children and Adults, *The American Journal of Cardiology,* by Mary J. Roman, MD,. Richard B. Devereux, MD, Randi Kramer–Fox, MS, and John O'Loughlin, MD. Sep. 1, 1989, pp. 507–512.

The Geometry of the Aortic Root in Health at Valve Disease and After ValveReplacement, *Journal of Biomechanics,* by H. Reul, A. Vahlbruch, M. Giersiepen, Th. Schmitz–Rode, V. Hirtz and S. Effert. vol. 23, No. 2, pp. 181–191 (1990).

Aortic Distensibility Abnormalities in Coronary Artery Disease, *American Journal of Cardiology,* by Christodoulos Stefanadis, MD, Charles F. Wooley, MD, Charles A. Bush, MD, Albert J. Kolibash, MD and Harisios Boudoulas., MD, pp. 1300–1304, 1987.-

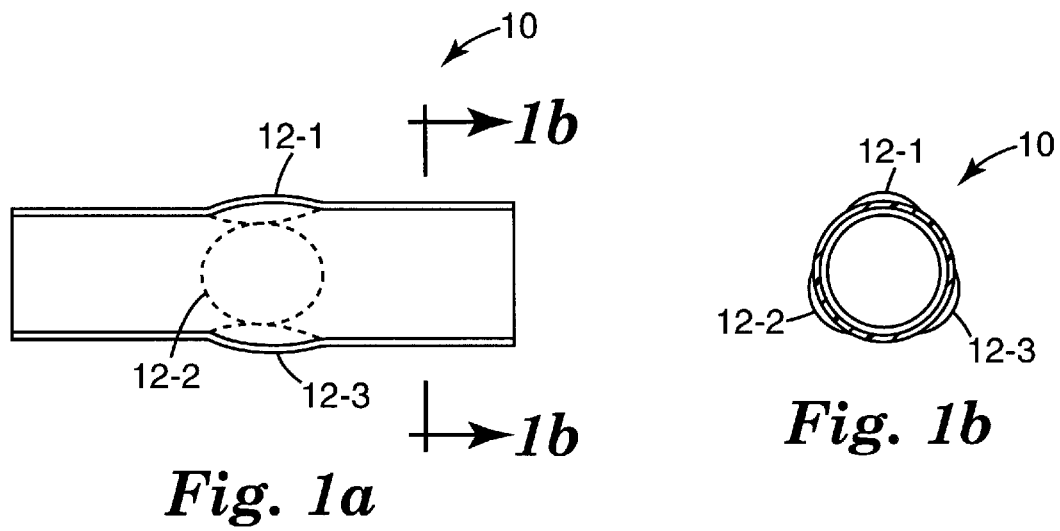
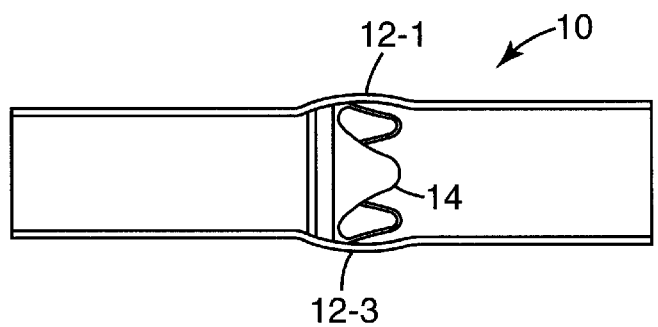
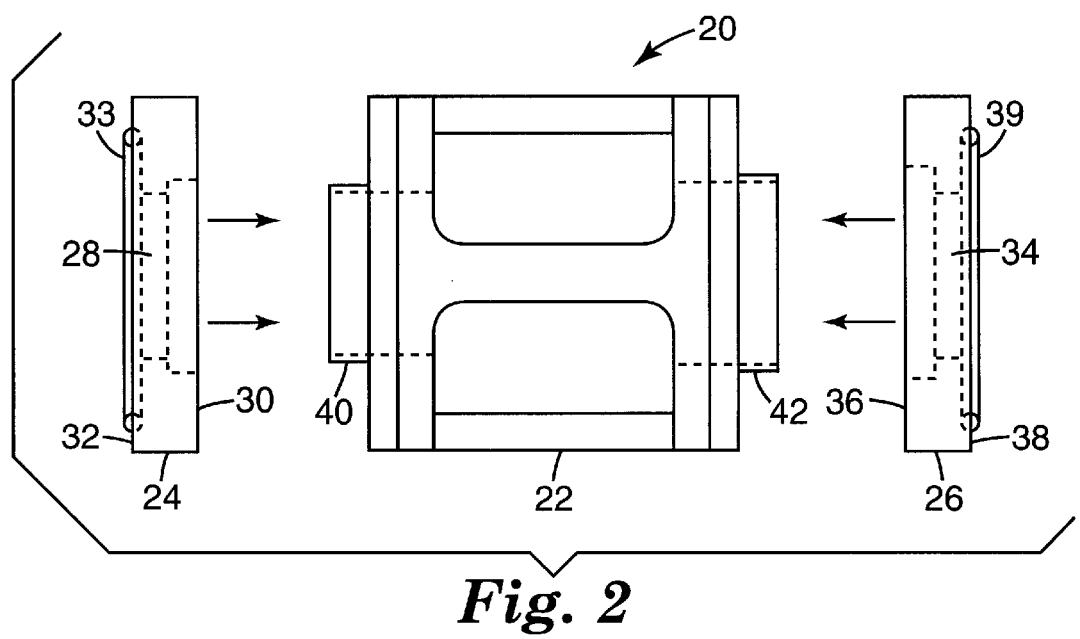

COMPLIANT SIMULATED AORTAS, METHOD FOR MAKING SAME BY ADJUSTING DUROMETER OF MATERIALS, AND METHOD FOR TESTING HEART VALVES

FIELD OF THE INVENTION

This invention relates generally to the field of bioprosthetic devices, and more particularly to a method and apparatus for in vitro testing of bioprosthetic valves.

BACKGROUND OF THE INVENTION

In the field of bioprosthetic devices, a wide variety of different aortic valve prostheses have been shown in the prior art. Two main categories of valve prostheses can be defined: mechanical valves, including the so-called "caged ball", "caged disc", and "tilting disc" types; and tissue valves, which have leaflets. Of the various aortic valve prostheses currently known, the mechanical valves tend to be more circumferentially rigid than tissue valves. Tissue valves are typically stented and tend to be more or less circumferentially rigid, depending upon the rigidity of the stent.

It is believed by the inventors, however, that valves less rigid than even the current stented tissue valves would be preferable in some cases since they more closely simulate a natural aortic valve and would therefore be less likely to create problems in the patient with unfavorable systolic and diastolic turbulence patterns, systolic pressure gradients, or embolic episodes. Further, it is believed that compliant bioprosthetic valves, having qualities more closely matched to natural aortic valves, would tend to have better flow efficiency, superior hydraulic characteristics, and flow patterns that are significantly less trauma-promoting and less likely to produce such undesirable effects as thrombus, atherosclerosis, or hemolysis.

The possibility of fatigue-related or other failure of the valve or leaflets has necessitated rigorous stress analysis and testing of bioprosthetic valves. Typically, the development of a bioprosthetic valve involves several iterations of the following steps: (1) fabrication of prototypes in various sizes; (2) in vitro (fluid-mechanical, structural, and fatigue) testing of the prototypes; and (3) refinement and re-fabrication.

Among the more common tests are: steady flow studies, which focus on the pressure gradients across the valves; pulsatile flow studies, which are concerned with valve dynamics (opening and closing times, leaflet motion, and the like), forward and backward (regurgitating) flow patterns, the pressure gradients across the valve, and energy loss across the valve; and fatigue studies, which are concerned with the ability of the valve to withstand millions of cycles without fatigue-related failure. These are discussed extensively in the literature.

Of course, it is important for the conditions of any in vitro testing of bioprosthetic devices to simulate, as closely as possible, the in vivo conditions to which the tested devices will be exposed upon implant in patients. In the case of mechanical valves and stented tissue valves, it is a simple matter to rigidly dispose a valve prosthesis, which is itself circumferentially rigid, along a fluid flow path for the purposes of testing. In conventional practice, a stented valve is fitted into a rigid valve holder and secured in place therein by means of a threaded retaining ring. The entire circumferentially rigid valve and valve holder can then be easily introduced into the flow path of various types of testing equipment.

It has been the inventors' experience that in the case of a non-stented valve, it is substantially more difficult to provide a fixture for introducing the non-stented tissue valve into a flow path during in vitro testing that, while providing support for the valve attachment to the tester, does not interfere with the physiological functioning of the valve. In particular, it is believed to be desirable to provide a test fixture for non-stented bioprosthetic valves which does not restrict the circumferential compliance of the valve, so that the effects of the valve's compliant circumferential expansion and contraction of the valve can be observed and monitored during the in vitro testing.

In addition, in vitro evaluation of non-stented aortic bioprostheses requires that the valve be mounted in a test chamber that reasonably simulates the human aortic root. The use of a simulated or synthetic aortic root has been proposed in the prior art. Artificial aortic roots have been discussed, for example, in Reul et al., "Optimal Design of Aortic Leaflet Prosthesis", *American Society of Civil Engineers, Journal of the Engineering Mechanics Division*, v. 104, n. 1, February 1978, pp. 91–117; in Ghista et al., "Optimal Prosthetic Aortic Leaflet Valve: Design Parametric and Longevity Analyses: Development of the Avcothane 51 ,Leaflet Valve Based on the Optimum Design Analysis", Journal of Biomechanics, 10/5–6, 1977 pp 313–324; and in Lu et al., "Measurement of Turbulence in Aortic Valve Prostheses: An Assessment by Laser Doppler Anemometer", *Proceedings of a Symposium at the 14th Annual Meeting of the Association for the Advancement of Medical Instrumentation,* Las Vegas, Nev. May 21, 1979, Yoganathan et al., editors. The foregoing Reul et al., Ghista et al., and Lu et al. references are incorporated herein by reference in their entirety. Such aortic roots have been made of polyurethane and silicone rubber.

In developing a simulated aorta for in vitro use, several factors must be considered. First, the aortic valve in its natural state does not have a fixed shape, and can only be described at a given time in the cardiac cycle, such as mid-systole or mid-diastole. Second, the human aorta is anisotropic and expands quite easily at low internal pressure but stiffens at higher pressures to prevent ballooning (this is discussed in Thubrikar et al., "Normal Aortic Valve Function in Dogs", *American Journal of Cardiology,* vol. 40, October 1977; in Brewer et al., "The Dynamic Aortic Root", *Journal of Cardiovascular Surgery,* Jun. 3, 1976; and in Ferguson et al., "Assessment of Aortic Pressure-Volume Relationships With an Impedance Catheter", *Catheterization and Cardiovascular Diagnosis,* 15:27–36, 1988). The foregoing Thubrickar et al., Brewer et al., and Ferguson et al. references incorporated herein by reference in their entirety. The compliance may vary with age and with disease states.

Finally, since in vitro evaluation of an aortic bioprosthesis requires extended testing, a material which provides bacterial stability is necessary. Materials such as rubber provide bacterial stability and can be easily produced to exact geometric dimensions, but these materials are isotropic and do not exhibit the same locking characteristics at high pressures that are seen with anisotropic materials. For these reasons, it would be advantageous to provide a simulated aorta of repeatable geometric design and having controllable compliance characteristics to provide reasonable in vitro models of natural aortas.

With the in vitro testing arrangement proposed by Lu et al. in the above-cited reference, the compliance factor for a flow loop system including a simulated aortic root is provided not by the simulated root itself, but rather by means of a compliance chamber disposed on the outflow side of the valve being tested. It would be desirable to provide the necessary compliance in the aorta itself for better simulation of the natural aorta.

In the above-cited Reul et al. and Ghista et al. references, the artificial aortic root is made from polyurethane by a dipping process, so that the desired compliance is achieved by controlling the thickness of the polyurethane at the time the artificial aorta is fabricated. (The Reul et al. flow loop additionally contains a compliance element for approximating natural compliance factors during testing.) The lack of consistency in the thickness of the root may pose difficulties. The trial and error effort required to develop aortas of the desired compliance would require large numbers of molds of different thicknesses, all very expensive to make, resulting in a very expensive, possibly a prohibitively expensive, development effort for valves produced commercially. Furthermore, the geometry (i.e., the thickness) of the simulated aorta will vary with each level of compliance so that test results performed at one compliance level may not be able to be accurately compared to those at other compliance levels.

SUMMARY OF THE INVENTION

In one aspect, the invention is a method of creating a simulated aorta patterned from a natural aorta and having a preselected amount of compliance comprising the following steps:
- selecting the dimensions of a simulated aortic root patterned according to the dimensions of a natural aorta;
- providing a mold for a simulated aorta of the desired dimensions;
- selecting the amount of circumferential compliance desired in the simulated aorta;
- selecting a material of appropriate durometer to provide the selected amount of circumferential compliance in a simulated aorta having the selected dimensions; and
- making the aorta by curing the material in the mold.

In this aspect, the material is preferably a polymer comprising an elastomer and a filler and the durometer of the material results from varying the proportions of the filler and the elastomer.

In another aspect, the invention is a group of simulated aortas prepared according to the above method, preferably comprised of materials of different Durometers so that the aortas have at least two different compliancies. Each aorta may have dimensions sized to receive one valve in a group of prosthetic valves of different sizes.

In another aspect, the invention is a method of testing non-stented valves comprising the following steps:
- selecting the dimensions of a simulated aortic root patterned according to the dimensions of a natural aorta;
- selecting the amount of circumferential compliance desired in the simulated aorta;
- selecting a material of appropriate durometer to provide the selected amount of circumferential compliance in a simulated aorta having the selected dimensions;
- making the aorta of the given dimensions by curing the material, and;
- placing a non-stented tissue valve having an outer diameter about the same size as the inner diameter of the simulated aorta within the aorta, and
- using the valve and aorta to test the performance of the valve to determine whether it can be recommended for use.

In this aspect, the method preferably includes the step of selecting the dimensions for simulated aortic roots of more than one size, the step of selecting the material includes the step of varying the durometer of a two-component material, and the testing step includes the step of testing more than one valve, each valve having the dimensions of a simulated aorta.

Other aspects and embodiments of the invention will be apparent to those of ordinary skill in the art.

BRIEF DESCRIPTION OF THE DRAWINGS

With the considerations such as are set forth in the foregoing discussion, the inventors will describe herein a method and apparatus for in vitro testing of circumferentially compliant bioprosthetic devices. Various aspects of the present invention will be best understood with reference to the following detailed description of specific embodiments of the invention, when read in conjunction with the accompanying drawings, wherein:

FIGS. 1a and 1b are side and end views, respectively, of a simulated aorta in accordance with one embodiment of the present invention, and FIG. 1c is a side view of the aorta from FIGS. 1a and 1b showing a bioprosthetic valve disposed therein;

FIG. 2 is an exploded side view of a test fixture in accordance with one embodiment of the present invention;

DETAILED DESCRIPTION OF SPECIFIC EMBODIMENTS OF THE INVENTION

Figure 3:
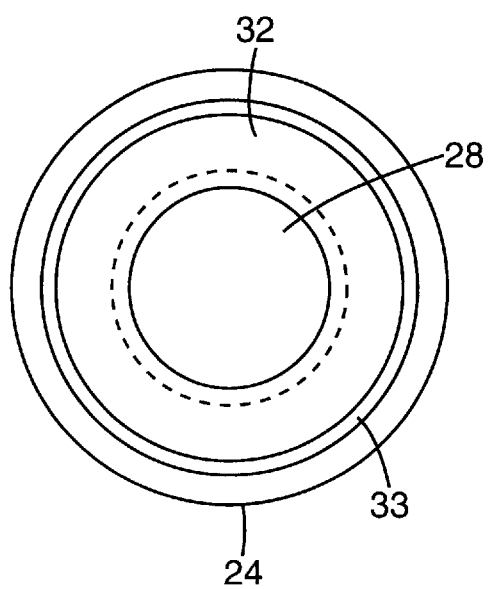
FIG. 3 is an end view of an end cap from the fixture of FIG. 2.

Referring to FIGS. 1a and 1b, there are shown side and end views, respectively, of a simulated aorta 10 in accordance with one embodiment of the present invention. In keeping with one aspect of the present invention, aorta 10 of FIGS. 1a and 1b is provided with three sinuses, 12-1, 12-2, and 12-3, which imitate the natural anatomy of a human aorta. Aorta 10 is, in the presently disclosed embodiment of the invention, approximately 10 cm long, and can be formed in various inner diameters, typically ranging between about 17 mm, preferably 19 mm to about 27 mm.

It will be appreciated that simulated aortas are provided in sizes to accommodate the valve to be tested, whatever size the valve may be. In the preferred embodiment, a group of aortas are prepared, having inner diameters at 2 mm intervals, ranging from 17 mm or 19 mm to 27 mm because the heart valves to be tested are produced with outer diameters of 17 mm (sometimes), 19 mm, 21 mm, 23 mm, 25 mm, and 27 mm for commercial use.

Simulated aorta 10 has been patterned from dimensional data available through published clinical literature. The geometry of aorta 10 is based upon the normal human adult aorta, as reported, for example, by Roman, et al in "Two Dimensional Echocardiographic Aortic Root Dimensions in Normal Children and Adults," *American Journal of Cardiology*, Sep. 1, 1989, P. 507, and by Reul et al., in "The Geometry of the Aortic Root in Health, at Valve Disease, and After Valve Replacement", *Journal of Biomechanics*, v. 23, n. 2, 1990, which articles are hereby incorporated by reference in their entirety. The dimensions for a normal aorta were chosen in the preferred embodiment rather than a diseased one, since the geometry of the diseased aorta varies as a result of the type and extent of the disease, as reported by Reul et al. and by Stefandadis, et al., "Aortic Distensibility Abnormalities in Coronary Artery Disease", *American Journal of Cardiology*, 59: 1300–1304, 1987, which article is hereby incorporated by reference in its entirety. By using a normal aorta as a model, a more normal distribution of the shape is reflected (see Reul et al.). Sizes based on measurements made with the leaflets in fully closed position were used because of the agreement in the literature on these dimensions.

Important dimensions are the depth and length of the sinuses and the diameter of the inflow and outflow sections. It should be noted from FIGS. 1a and 1c that one end of aorta 10, hereinafter referred to as the "inflow end", has a slightly smaller diameter than the other end, hereinafter referred to as the "outflow end", and the inflow end diameter should correspond with the valve's outer diameter.

As discussed earlier, the natural aorta has a certain elastic compliance which will vary, and that compliance of the natural aorta is one of the characteristics to be replicated. Data on compliance is found in the above-mentioned articles and was utilized to determine desirable compliancy for the simulated aorta. For example, 12–20% compliance (i.e., 16%±4%) over a 40 mmHg change in pressure is commonly described as normal compliance for the human aorta. 3–5% (i.e., 4%±1%) compliance over a 40 mmHg change in pressure is frequently found in elderly patients or those with disease states resulting in rigid aortas. Both of these compliance ranges have been set forth in the FDA guidelines for testing. Both ranges are utilized in preferred aortas of the present invention.

In order that simulated aorta 10 is reproduced with consistent and repeatable geometry and dimensions, a steel compression mold is produced for each size aorta. This mold controls all the above-mentioned dimensions as well as the thickness of the aorta. Thus, in the preferred embodiment, only 5 or 6 molds are produced. It will be appreciated that by way of this invention aortas of numerous compliancies can be produced using the same molds. Using these compliancies, disease states and normal states can be simulated and valves tested for use in these various conditions.

Aorta 10 is preferably made of a silicone elastomer with a silica filler. As would be appreciated by those of ordinary skill in the materials sciences, the silicone rubber can be formulated by varying the proportions of the elastomer and the filler to provide cured material of varying Durometers, and, in fact, such material is commercially available at different Durometers. By further mixing the commercially available material, almost any desired Durometer can be obtained. For a given thickness of material (which in the present invention is fixed by the compression mold), the specific Durometer of material will govern the compliance of the aorta. By trying different Durometers and using motion analysis testing (or other measurements of compliance of the simulated aorta), the Durometer necessary to produce the desired compliance for the desired aorta thickness necessary was determined. Thus, by carefully controlling the proportions of ingredients in the silicone rubber, the compliance of a simulated aorta made therefrom can be precisely selected with a high degree of precision and consistency. In the presently disclosed embodiment of the invention, aorta 10 is preferably molded using material of the specific Durometers mentioned below and cured for 24 hours to stabilize the material.

Results from the inventors' simulated aorta characterization studies show that simulated aortas such as aorta 10 in accordance with the presently disclosed embodiments of the invention, compression molded using the preferred material of 35 to 40 Durometer provided a consistent compliance level for each of the various sizes of aorta mentioned above. In particular, the aortas demonstrated a compliance quantified as a 4%±1% diameter change per 40 mmHg pressure change, and remained within these limits over a pressure range of 40 to 200 mmHg. Similarly aortas made of the same material with a Durometer of about 20 have a compliance of about 16%±4% diameter change per 40 mmHg pressure change, and also generally remained within these limits over a pressure range of 40–200 mmHg.

In FIG. 1c, simulated aorta 10 is shown having a bioprosthetic valve 14 disposed therein. Valve 14 is mounted in simulated aorta 10 by suturing the valve base and commissure tips, in accordance with known techniques in the art. Suture holes are preferably filled with ordinary liquified silicone rubber which is allowed to cure prior to testing, in order to prevent leakage of the aorta when it is disposed in a sealed test flow loop. As can be appreciated by those of ordinary skill in the art, the configuration shown in FIG. 1c provides minimal support for valve 14, and allows circumferential compliance during testing. Simulated aorta 10 does not interfere with the physiological functioning of the valve.

Although a particular type of valve 14 is depicted inside simulated aorta 10 in FIG. 1c, it is to be understood that this is done for the purposes of illustration only. Many different types of valves, whether they are mechanical or tissue valves, stented or non-stented, circumferentially rigid or circumferentially compliant, may be effectively tested using the method and apparatus of the present invention. The preferred valve, of course, is a non-stented tissue valve because the present invention allows evaluation of the advantages of a circumferentially non-rigid valve.

Figure 4:
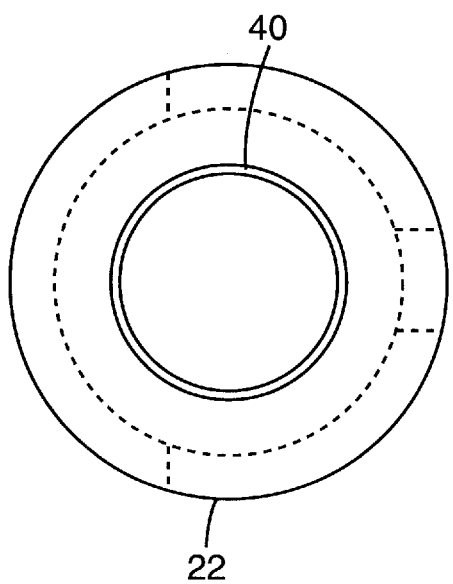
FIG. 4 is an end view of a central cradle portion of the fixture of FIG. 2.

Turning now to FIG. 2, an exploded view of a fixture 20 for supporting aorta 10 in accordance with one embodiment of the present invention is shown. Fixture 20 of FIG. 2 comprises three parts: a substantially cylindrical cradle portion 22, a substantially circular inflow end cap 24, and a substantially circular outflow end cap 26. An end view of inflow end cap 24 is shown in FIG. 3, and an end view of cradle 22 is shown in FIG. 4. Inflow end cap 24 and outflow end cap 26 are adapted to be fitted onto the inflow end and outflow end, respectively, of cradle 22, as will be hereinafter shown with reference to later figures. In particular, inflow end cap 24 has a circular opening 28 therethrough, with circular opening 28 having a slightly enlarged diameter on inner face 30 as compared to the diameter of opening 28 on the outer face 32 of cap 24. Similarly, outflow end cap 26 has a circular opening 34 therethrough, where opening 34 has a slightly larger diameter on the inner face 36 of cap 26 than on the outer face 38 of cap 26.

With continued reference to FIGS. 2 and 3, a rubber O-ring 33 is inset in the outer face 32 of inflow end cap 24. A similar O-ring 39 is inset in the outer face 38 of outflow end cap 26. As will become hereinafter apparent with reference to later figures, O-rings 33 and 39 enable fixture 20, once assembled in the manner to be hereinafter described, to be fitted into the flow loop of various test equipment such that the flow loop remains sealed.

Cradle 22 is provided with a cylindrical rim 40 on its inflow end, where the diameter of rim 40 is slightly smaller than the enlarged inner diameter of hole 28 in inflow end cap 24. Likewise, a cylindrical rim 42 disposed on the outflow end of cradle 22 has a diameter slightly smaller than the enlarged inner diameter of hole 34 in outflow end cap 26.

It should also be noted from FIG. 2 that the diameter of cylindrical rim 42 is somewhat larger than the diameter of cylindrical rim 40, and that the enlarged inner diameter of hole 34 in outflow end cap 26 is somewhat larger than the enlarged inner diameter of hole 28 in inflow end cap 24. The size differential between rim 42 and rim 40, and the corresponding size differential of holes 34 and 28 in respective end caps 26 and 24 is necessary due to the similar size differential between the outflow and inflow ends of simulated aorta 10, as previously noted with reference to FIGS. 1a and 1c.

Figure 5:
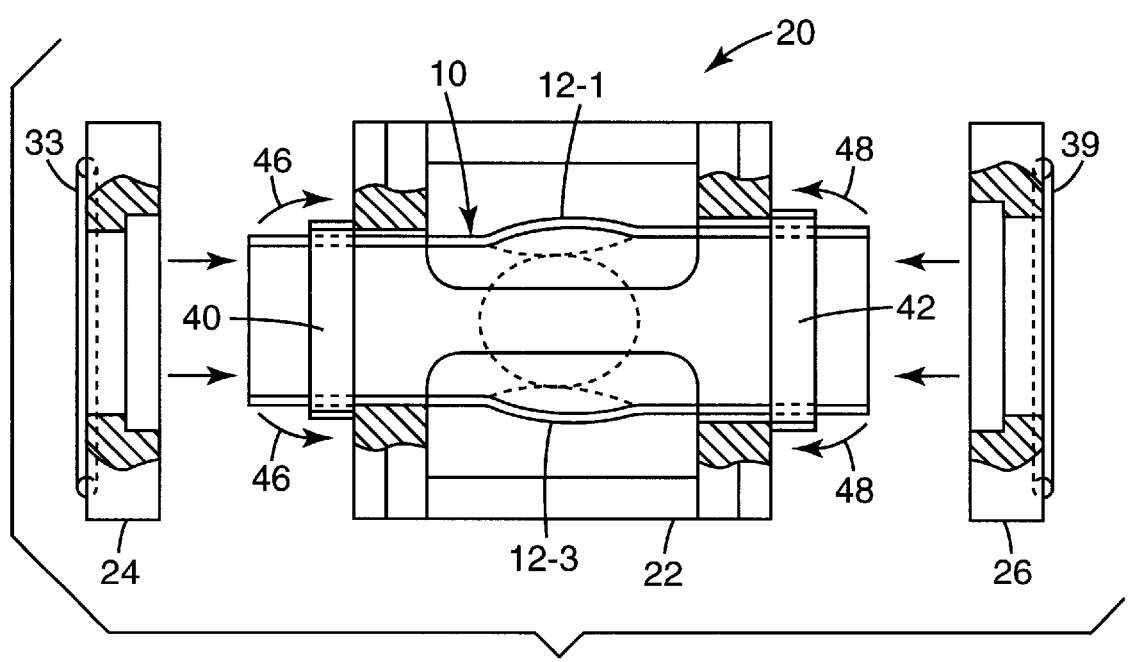
FIG. 5 is a partially cut-away exploded side view of the fixture of FIG. 2 having the aorta of FIGS. 1a, 1b, and 1c disposed therein.

With reference now to FIG. 5, a partially cut-away, exploded view of fixture 20 is shown, with aorta 10 from FIGS. 1a, 1b, and 1c having been inserted axially through the center of cradle 22. It is to be understood that prior to the insertion of simulated aorta 10 into cradle 22, a bioprosthetic valve, not shown in FIG. 5, is affixed inside simulated aorta 10, generally in the area of sinuses 12-1, 12-2, and 12-3, as previously described with reference to FIG. 1c. Once simulated aorta 10 has been inserted into cradle 22, the next stage in the process of assembling fixture 20 is to fold the inflow end of simulated aorta 10 back over cylindrical rim 40, in the direction indicated by arrows 46. Next, the outflow end of simulated aorta 10 is similarly folded back over cylindrical rim 42, in the direction indicated by arrows 48 in FIG. 5.

Figure 6:
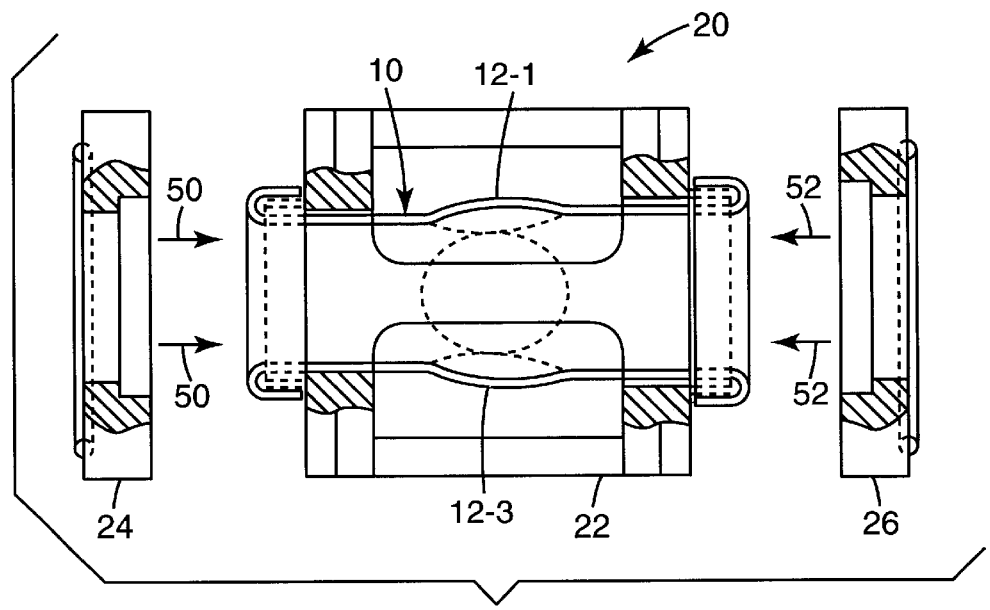
FIG. 6 is a partially cut-away exploded side view of the fixture and aorta from FIG. 5, wherein the aorta has been folded over a portion of the fixture.
Figure 7:
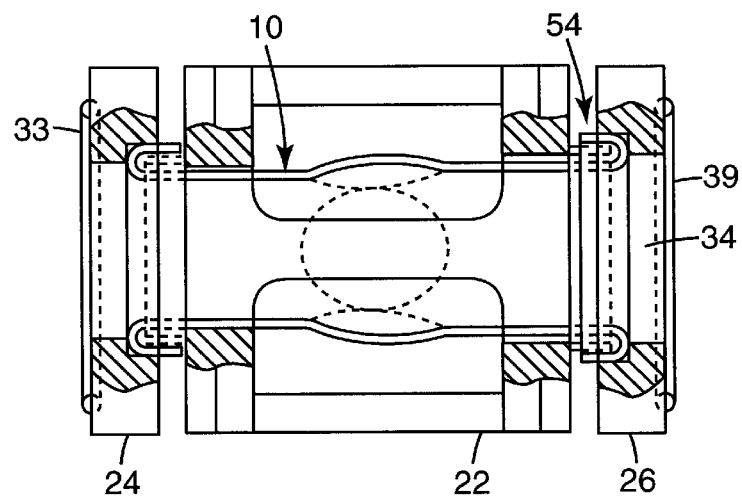
FIG. 7 is a partially cut-away side view of the fixture and aorta from FIGS. 5 and 6, fully assembled.
Figure 8:
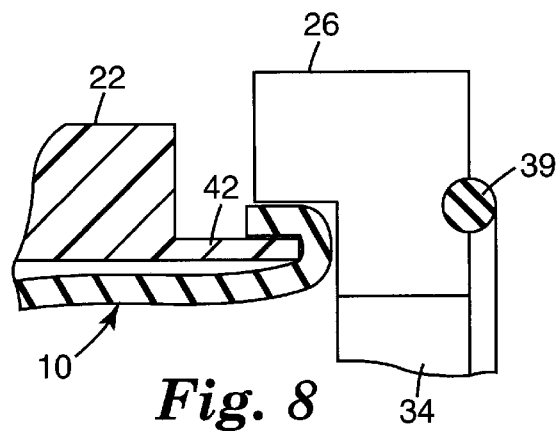
FIG. 8 is a greatly enlarged cross-sectional view of a portion of the fixture and aorta from FIG. 7.

Fixture 20 and simulated aorta 10, after the respective ends of aorta 10 are folded over rims 40 and 42, are depicted in FIG. 6. The next stage in the process of assembling fixture 20 and simulated aorta 10 is to fit end caps 24 and 26 onto the respective ends of cradle 22. In particular, inflow end cap 24 is pushed onto the inflow end of cradle 22, in the direction indicated by arrows 50 in FIG. 6. Fixture 20 and simulated aorta 10, after the respective end caps 24 and 26 have been fitted onto cradle 22, are depicted in FIG. 7. As can be seen from FIG. 7, the slightly larger inner diameter of respective holes 28 and 34 in caps 24 and 26 permits caps 24 and 26 to fit over the folded-over ends of simulated aorta 10, compressing the folded-over ends of simulated aorta 10 against rims 40 and 42 on cradle 22. A greatly enlarged view of the area denoted generally as 54 in FIG. 7 is shown in FIG. 8.

Figure 9:
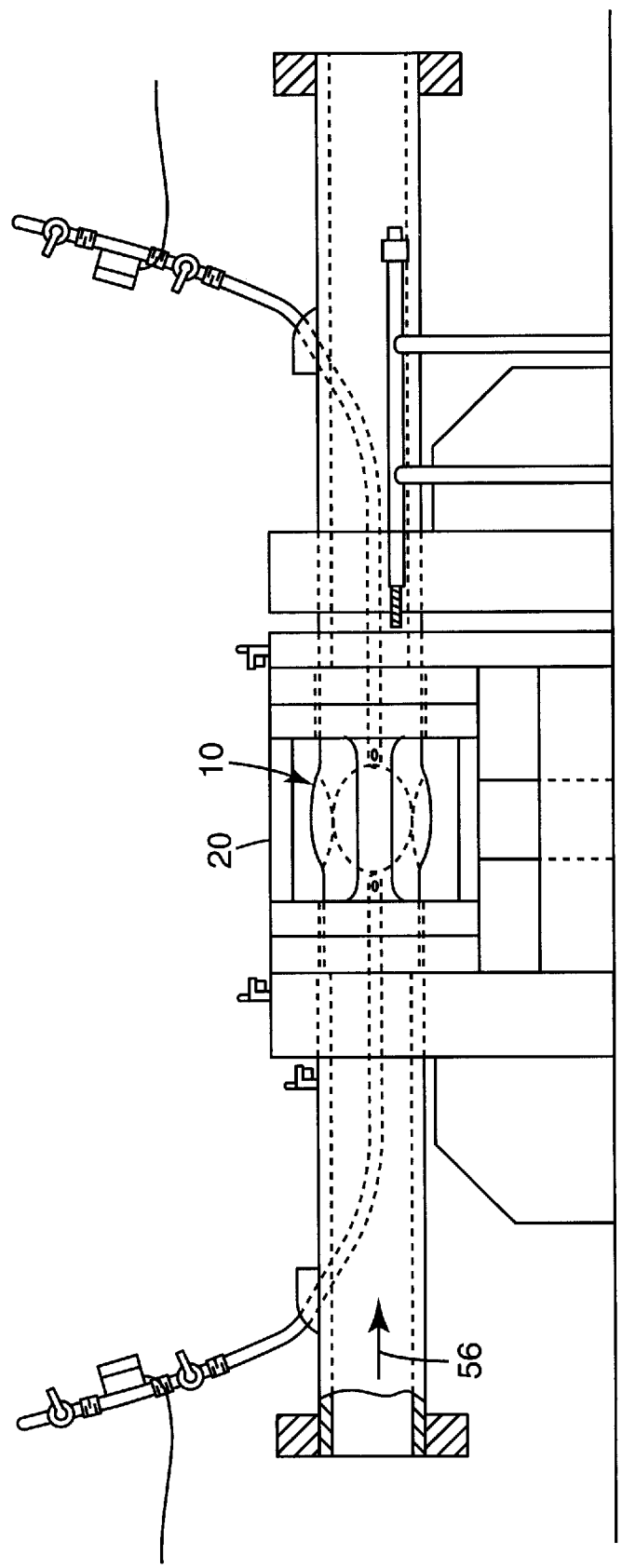
FIG. 9 is a side view of a test apparatus containing the aorta and fixture of FIG. 7.

Once assembled as shown in FIG. 7, fixture 20 provides support for aorta 10 and the bioprosthetic valve therein, without affecting the compliance of simulated aorta 10 in the area of sinuses 12-1, 12-2, and 12-3. By way of illustration, there is shown in FIG. 9 the assembled fixture 20 and simulated aorta 10 having been inserted into the flow loop of a pulsatile flow study apparatus, through which fluid flow is established in the direction indicated by arrow 56. In accordance with one aspect of the present invention, and as would be appreciated by those of ordinary skill in the art, fixture 20 and aorta 10 can be inserted and removed from various flow-loop apparatuses such as that shown in FIG. 9 without damage to aorta 10 and the bioprosthetic valve therein. In this way, the same simulated aorta/bioprosthetic valve combination can be subjected to a succession of different tests involving different flow loop apparatuses. Since the same aorta/valve combination can be used, the results from each one of the individual tests can be meaningfully and accurately correlated with the results from others in the succession of tests. As previously noted, this would not be possible if a different aorta/valve combination were used for each one of the tests.

Figure 10:
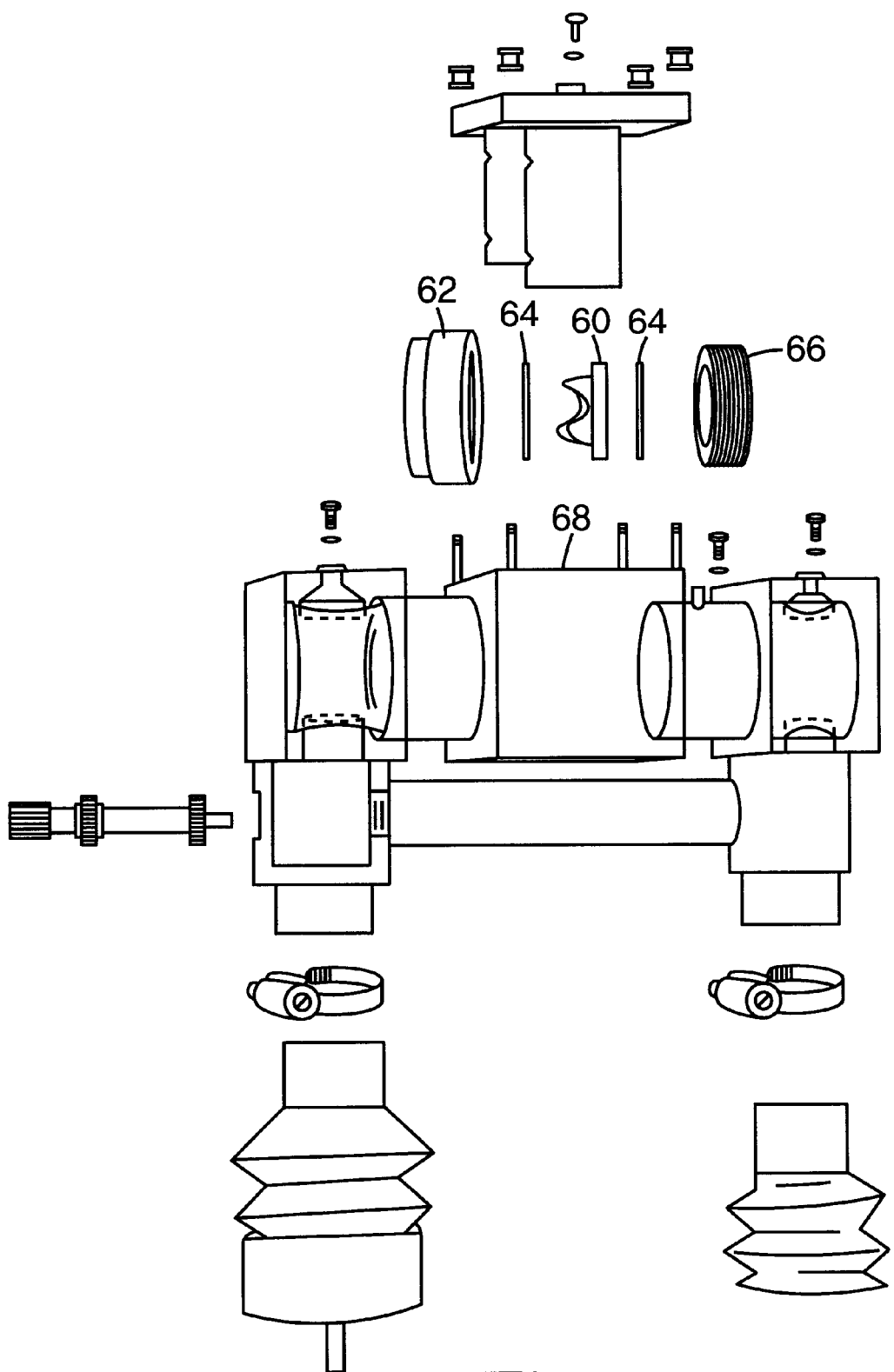
FIG. 10 is an exploded front view of a Shelhigh fatigue tester test chamber assembly of the prior art.

Turning now to FIG. 10, an exploded view of a test chamber assembly from a commercially-available Shelhigh 300™ Fatigue Test System is shown. The configuration shown in FIG. 10 is a conventional one, commonly utilized in the prior art for the purposes of fatigue testing of a stented (i.e., circumferentially rigid) bioprosthetic valve. In particular, a stented valve 60 is shown in FIG. 10. In accordance with the manufacturer's instructions, stented valve 60 is supported in the Shelhigh tester by means of a rigid valve holder 62. Retaining rings 64 are positioned on the inflow and outflow sides of valve 60, and retaining rings 64 and valve 60 are secured in valve holder 62 by a threaded ring 66. Valve holder 62 with valve 60 secured therein is then received in a test chamber 68, which holds valve holder 62 in the flow loop of the tester.

It is believed that other components of the Shelhigh test chamber assembly depicted in FIG. 10 would be familiar to those of ordinary skill in the art, and that such other components are not relevant to the present description of a particular embodiment of the invention. Accordingly, certain components of the test chamber assembly depicted in FIG. 10 will not be described herein in detail.

As would be further appreciated by those of ordinary skill in the art, the fatigue testing arrangement depicted in FIG. 10 is not entirely suitable for the purposes of testing non-stented or otherwise circumferentially compliant valves, since the rigidity of valve holder 62 would prevent circumferential expansion or contraction of the valve being tested, and would therefore prevent the investigator from obtaining reliable data concerning operation of the valve being tested.

In accordance with another feature of the presently disclosed embodiment of the invention, therefore, there is provided an adaptation of the test chamber assembly of FIG. 10 that allows a non-stented, circumferentially compliant valve to be supported in the flow loop of the Shelhigh tester in a manner that allows for the effects of the valve's circumferential compliance to be accounted for in the course of the fatigue testing. In particular, and as shown in FIG. 11, the adaptation of the Shelhigh tester to accommodate compliant valves involves simulated aorta 10 previously described in detail with reference to FIGS. 1a, 1b, and 1c.

Figure 11:
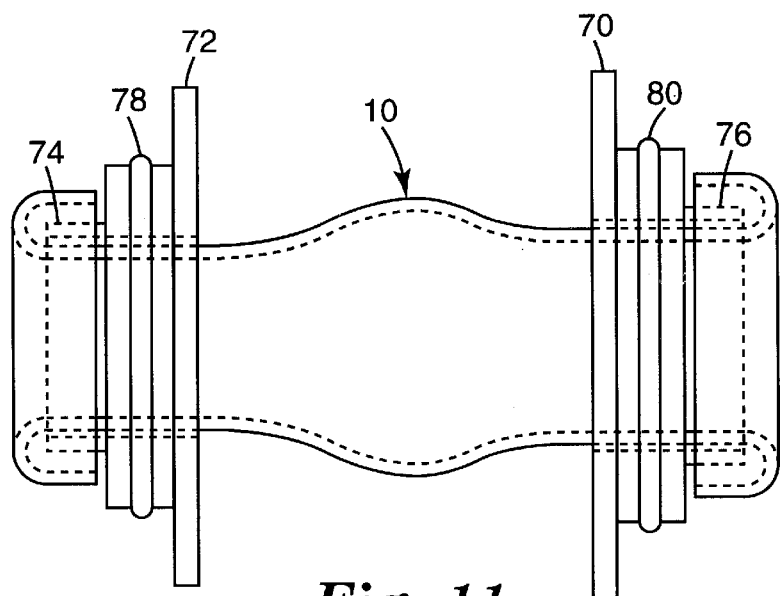
FIG. 11 is a side view of the aorta of FIGS. 1a, 1b, and 1c having adapter rings in accordance with one embodiment of the present invention attached thereto.

Simulated aorta 10 in FIG. 11 is introduced into the flow loop of the Shelhigh tester by means of an adapter ring 70 on the inflow side of aorta 10 and an adapter ring 72 on the outflow side of aorta 10. In accordance with the presently disclosed embodiment of the invention, adapter rings 70 and 72 are preferably capable of being received in test chamber 68 in place of the prior art valve holder assembly, including valve holder 62, retaining rings 64, and threaded ring 66.

Figure 12A:
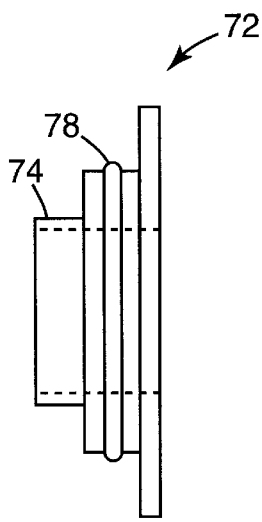
FIGS. 12a and 12b are side and end views, respectively of one of the adapter rings from FIG. 11.
Figure 12B:
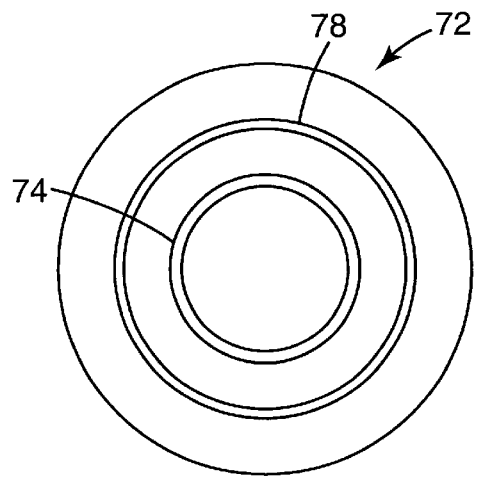

A side view of adapter ring 72 is shown in FIG. 12a, and an end view of adapter ring 72 is shown in FIG. 12b. Adapter ring 72 is provided with a cylindrical rim 74 that functions in much the same manner as cylindrical rims 40 and 42 in the embodiment of the present invention previously described with reference to FIG. 5. Of course, adapter ring 70 is similarly provided with a cylindrical rim, designated as 76 in FIG. 11. Adapter rings 72 and 70 are further provided with O-rings 78 and 80, respectively, which function to establish a seal between adapter rings 72 and 70 and test chamber 68 of the Shelhigh tester.

Figure 13:
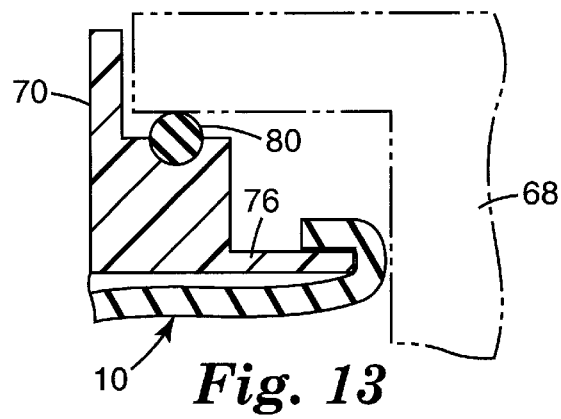
FIG. 13 is a greatly enlarged cross sectional view of part of the aorta and adapter ring from FIG. 11.

A greatly enlarged cross-sectional view of a portion of adapter ring 70 is provided in FIG. 13. The inflow end of simulated aorta 10 is folded around cylindrical rim 76 in the same manner as the ends of aorta 10 were folded around cylindrical rims 40 and 42 in the embodiment of the invention previously described with reference to FIG. 5. O-ring 80 forms a seal between adapter ring 70 and the inflow side of test chamber 68, which is shown in phantom in FIG. 13. It is to be understood of course that simulated aorta 10 is similarly coupled to adapter ring 72 on the outflow side of test chamber 68.

Once the aorta and fixture are coupled to this and other testing apparatus, testing of the valve is completed and evaluated in conventional fashion.

From the foregoing detailed description of specific embodiments of the present invention, it should be apparent that a method for producing a simulated aorta, a group of such aortas and a method for testing a circumferentially compliant valve has been disclosed. Although particular embodiments of the invention have been described herein in some detail, this has been done for the purposes of illustration only, and is not intended to be limiting with respect to the scope of the invention as defined in the appended claims which follow. It has been contemplated by the inventors that various changes, alterations, or modifications may be made to the invention as described herein without departing from the spirit and scope of the invention as defined in the claims.

What is claimed is:

1. A method of creating a simulated aorta for use in in vitro testing of an aortic valve, the simulated aorta patterned from a natural aorta and having a preselected amount of compliance comprising the following steps:

selecting the dimensions of a simulated aortic root patterned according to the dimensions of a natural aorta;

providing a mold for a simulated aorta of the desired dimensions;

selecting the amount of circumferential compliance desired in the simulated aorta;

selecting a material of appropriate durometer to provide the selected amount of circumferential compliance in a simulated aorta having the selected dimensions;

making the simulated aorta by curing the material in the mold, the simulated aorta being suitable for use in testing of an aortic valve.

2. A method according to claim 1 and wherein the material is a polymer comprising an elastomer and a filler.

3. A method according to claim 2 and where the durometer of the material results from varying the proportions of the filler and the elastomer.

4. A group of simulated aortas prepared according to the method of claim 1.

5. A group of simulated aortas prepared according to the method of claim 2, using materials of at least two different durometers to produce simulated aortas of at least two different compliancies.

6. A group of simulated aortas prepared according to the method of claim 4, each simulated aorta having dimensions sized to receive one size valve in a group of prosthetic valves of different sizes.

7. A method of testing non-stented valves comprising the following steps:

selecting the dimensions of a simulated aortic root patterned according to the dimensions of a natural aorta;

selecting the amount of circumferential compliance desired in the simulated aorta;

selecting a material of appropriate durometer to provide the selected amount of circumferential compliance in a simulated aorta having the selected dimensions;

making the aorta of the given dimensions by curing the material;

placing a non-stented tissue valve having an outer diameter about the same size as the inner diameter of the simulated aorta within the aorta; and using the valve and aorta to test the performance of the valve to determine whether it can be recommended for use.

8. A method according to claim 7 and wherein the step of selecting the dimensions includes the step of selecting the dimensions for simulated aortic roots of more than one size, the step of selecting the material includes the step of varying the durometer of a single material, and the testing step includes the step of testing more than one valve, each valve having the dimensions of a simulated aorta.

9. The method of claim 1, wherein the simulated aorta is a simulated aortic root.

10. The method of claim 1, further comprising:
    providing the simulated aorta with three sinuses.

11. The method of claim 1, further comprising:
    forming the simulated aorta to a length of approximately 10 cm.

12. The method of claim 5, wherein the simulated aortas of at least two different compliancies have corresponding thicknesses.

13. The method of claim 5, wherein a single mold is used to produce the simulated aortas of at least two different compliancies.

* * * * *